(12) United States Patent
Lee et al.

(10) Patent No.: US 9,739,764 B2
(45) Date of Patent: Aug. 22, 2017

(54) SENSOR STRIP CARTRIDGE, AND BIOMETRIC INFORMATION MEASURING METHOD AND APPARATUS USING THE SAME

(71) Applicant: SAMSUNG ELECTRONICS CO., LTD., Suwon-si (KR)

(72) Inventors: Min-hyoung Lee, Seongnam-si (KR); In-geol Baek, Icheon-si (KR); Seong-je Cho, Icheon-si (KR); Chul-ho Cho, Seongnam-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 240 days.

(21) Appl. No.: 14/444,228

(22) Filed: Jul. 28, 2014

(65) Prior Publication Data

US 2015/0028097 A1  Jan. 29, 2015

(30) Foreign Application Priority Data

Jul. 26, 2013  (KR) .......................... 10-2013-0088980

(51) Int. Cl.
  *G06F 17/00* (2006.01)
  *G01N 33/49* (2006.01)
  *G01N 33/487* (2006.01)

(52) U.S. Cl.
  CPC ....... *G01N 33/49* (2013.01); *G01N 33/48771* (2013.01)

(58) Field of Classification Search
  USPC ........................................................ 235/375
  See application file for complete search history.

(56) References Cited

U.S. PATENT DOCUMENTS

| | | | |
|---|---|---|---|
| 7,695,608 B2 | 4/2010 | Kim et al. | |
| 8,277,635 B2 | 10/2012 | Kim et al. | |
| 8,314,613 B2 * | 11/2012 | Cui ................. | G01N 33/48771 204/403.01 |
| 8,377,272 B2 | 2/2013 | Kim et al. | |
| 2003/0124738 A1 * | 7/2003 | Crosby ............... | G01N 33/558 436/514 |
| 2007/0231209 A1 * | 10/2007 | Cosentino ........ | G01N 33/48771 422/68.1 |

(Continued)

FOREIGN PATENT DOCUMENTS

| | | |
|---|---|---|
| JP | 2002-196003 A | 7/2002 |
| JP | 2007-11559 A | 1/2007 |

(Continued)

*Primary Examiner* — Rafferty Kelly
(74) *Attorney, Agent, or Firm* — Sughrue Mion, PLLC (57) ABSTRACT

A sensor strip cartridge and a biometric information measuring method and apparatus using the same are provided. The biometric information measuring apparatus includes a cartridge accommodator configured to accommodate a sensor strip cartridge including at least one sensor strip, a cartridge information reader configured to read cartridge information about the sensor strip cartridge from the sensor strip cartridge, a controller configured to receive biometric information through the sensor strip, and correct the received biometric information by using a biometric information correction reference corresponding to the cartridge information, and an outputter configured to output the corrected biometric information.

14 Claims, 8 Drawing Sheets

(56) References Cited

U.S. PATENT DOCUMENTS

2013/0027064 A1* 1/2013 Austera ............ G01N 27/3272
                                                          324/692
2014/0000389 A1    1/2014 Ohtsuka et al.

FOREIGN PATENT DOCUMENTS

| JP | 2012-185138 A    | 9/2012  |
|----|------------------|---------|
| KR | 10-0854389 B1    | 8/2008  |
| KR | 10-2008-0080841 A | 9/2008 |
| KR | 10-0874158 B1    | 12/2008 |
| KR | 10-0874159 B1    | 12/2008 |
| KR | 10-0896234 B1    | 5/2009  |
| KR | 10-1149818 B1    | 5/2012  |

* cited by examiner

SENSOR STRIP CARTRIDGE, AND BIOMETRIC INFORMATION MEASURING METHOD AND APPARATUS USING THE SAME

CROSS-REFERENCE TO RELATED APPLICATION

This application claims priority from Korean Patent Application No. 10-2013-0088980, filed on Jul. 26, 2013 in the Korean Intellectual Property Office, the disclosure of which is incorporated herein in its entirety by reference.

BACKGROUND

1. Field

Apparatuses and methods consistent with exemplary embodiments relate to a sensor strip cartridge and a biometric information measuring method and apparatus using the sensor strip cartridge, and more particularly, to a sensor strip cartridge and a biometric information measuring method and apparatus using the sensor strip cartridge whereby information about a sensor strip is automatically recognized.

2. Description of the Related Art

The number of patients having various diseases has increased due to changes in eating habits and lack of exercise. For example, the number of patients having type II diabetes mellitus has increased. In such diabetic patients, periodic blood sugar management is very important. An electrochemical biometric information measuring apparatus, which is easy to carry, is frequently used for periodic blood sugar management.

The portable electrochemical biometric information measuring apparatus may measure biometric information by using a strip type bio sensor (hereinafter also referred to as a sensor strip). In this case, the sensor strip has to be replaced each time the biometric information is measured.

A cartridge type product including a plurality of sensor strips accommodated in one case has been recently introduced in order to increase a user's convenience. In this case, a sensor strip is replaced each time a user measures his or her biometric information.

Although numerical values indicated by sensor strips should be almost the same, deviations between such values appear depending on a manufacturing date and manufacturing lot number. Therefore, the numerical value indicated by the sensor strip has to be corrected by using a correction reference corresponding to the manufacturing lot number of the sensor strip. In the related art, a user assigns a manufacturing lot number of a sensor strip to a biometric information measuring apparatus in order to correct a numerical value indicated by the sensor strip.

SUMMARY

One or more exemplary embodiments provide a sensor strip cartridge and a biometric information measuring method and apparatus using the sensor strip cartridge whereby information about a sensor strip is automatically recognized.

Further, one or more exemplary embodiments provide a sensor strip cartridge and a biometric information measuring method and apparatus using the sensor strip, whereby information about a sensor strip is automatically recognized even when a user does not directly input production information of a sensor strip corresponding to a correction reference for measured biometric information.

Further still, one or more exemplary embodiments provide a sensor strip cartridge and a biometric information measuring method and apparatus using the sensor strip cartridge, which increase a user's convenience when using a biometric information measuring apparatus including a sensor strip.

Further still, one or more exemplary embodiments provide a sensor strip cartridge and a biometric information measuring method and apparatus using the sensor strip cartridge, whereby an error in biometric information is prevented from occurring due to an input error in manufacturing information of a sensor strip when a biometric information measuring apparatus is used.

According to an aspect of an exemplary embodiment, there is provided a biometric information measuring apparatus including: a cartridge accommodator configured to accommodate a sensor strip cartridge including at least one sensor strip; a cartridge information reader configured to read cartridge information about the sensor strip cartridge from the sensor strip cartridge; a controller configured to receive biometric information through the sensor strip, and correct the received biometric information by using a biometric information correction reference corresponding to the cartridge information; and an outputter configured to output the corrected biometric information.

The cartridge information reader may include a short-distance communication device, and the short-distance communication device may be configured to receive the cartridge information stored in the sensor strip cartridge from the sensor strip cartridge.

The cartridge information reader may include one or more devices selected from a barcode reader device or a quick response (QR) code reader device, and the cartridge information reader may be configured to read the cartridge information, which is converted into a barcode or a QR code and stored in the sensor strip cartridge, from the sensor strip cartridge.

The cartridge information reader may include a color sensor, and the color sensor may be configured to sense the cartridge information, which is converted into a color band including at least one or more colors and stored in the sensor strip cartridge, from the sensor strip cartridge.

The cartridge information reader may include: an emitter that is provided to face a first surface of a light transmitting layer included in the sensor strip cartridge and is configured to emit light; and a light receiver that is provided to face a second surface of the light transmitting layer, the second surface being opposite to the first surface, and may be configured to receive the light which is emitted from the emitter and passes through the light transmitting layer.

At least one portion of the light transmitting layer may include blocked portions which do not transmit the light based on the cartridge information, and the cartridge information reader may be configured to detect the blocked portions of the light transmitting layer to thereby read the cartridge information.

The cartridge information reader may include: an emitter that is provided to face a surface of a light reflecting layer included in the sensor strip cartridge and configured to emit light; and a light receiver configured to receive the light which is emitted from the emitter and reflected by the light reflecting layer.

At least one portion of the light reflecting layer may include blocked portions which do not reflect light based on the cartridge information, and the cartridge information reader may be configured to detect the blocked portions to thereby read the cartridge information.

The sensor strip cartridge may include an electrode that is disposed in a portion of the sensor strip cartridge based on the cartridge information, and the cartridge information reading unit may be configured to include two or lines that extend toward the sensor strip cartridge. The cartridge information reader may be configured to apply a voltage to only a first line among the two lines, detect whether the voltage is applied to a second line among the two lines, by the first line and the electrode, and thereby detect a position of the sensor strip cartridge where the electrode is disposed, and read the cartridge information by using the detected position.

The cartridge information reader may include: a voltage source that is connected to one end of a resistor included in the sensor strip cartridge, and may be configured to apply a voltage to the resistor; a reference resistor that is connected to the other end of the resistor at one end of the reference resistor, and is connected to a ground at the other end of the reference resistor; and an analog-to-digital converter (ADC) that is connected to the other end of the resistor, and the resistor has a value corresponding to the cartridge information.

The cartridge information reader may be configured to read the cartridge information via a level of a voltage detected through the ADC.

The sensor strip cartridge may include a protrusion which is disposed in at least one portion of the sensor strip cartridge based on the cartridge information, and the cartridge information reader may include at least one or more switches. The cartridge information reader may be configured to detect a switch of the at least one or more switches which contacts the at least one protrusion, detect a position of the sensor strip cartridge where the at least one protrusion is disposed based on the detecting the switch, and read the cartridge information by using the detected position.

According to an aspect of another exemplary embodiment, there is provided a biometric information measuring method including: accommodating a sensor strip cartridge in a biometric information measuring apparatus; reading, by the biometric information measuring apparatus, cartridge information about the sensor strip cartridge from the sensor strip cartridge; acquiring a biometric information correction reference corresponding to the read cartridge information; receiving biometric information through a sensor strip included in the sensor strip cartridge; correcting the biometric information by using the biometric information correction reference; and outputting the corrected biometric information.

According to an aspect of another exemplary embodiment, there is provided a sensor strip cartridge including: a case; at least one sensor strip that is accommodated in the case; and a cartridge information storage configured to store cartridge information about the at least one sensor strip.

The cartridge information may include manufacturing information of the at least one sensor strip.

The cartridge information may include at least one or more type of information selected from a manufacturing date, an expiration date, a manufacturing lot number, and an identification code of the at least one sensor strip.

The cartridge information storage may include a light transmitting layer that is provided in the case, at least one portion of the light transmitting layer may include blocked portions which do not transmit light, and positions of the blocked portions may correspond to the cartridge information.

The cartridge information storage may include a light reflecting layer that is provided in the case, at least one portion of the light reflecting layer may include blocked portions which do not transmit light, and positions of the blocked portions may correspond to the cartridge information.

The cartridge information storage may include at least one electrode that is provided in the case, and a position where the at least one electrode is provided may correspond to the cartridge information.

The cartridge information storage may include a resistor, and the resistor may have a value corresponding to the cartridge information.

The cartridge information storage may include at least one protrusion that is provided in the case, and a position where the at least one protrusion is provided may correspond to the cartridge information.

BRIEF DESCRIPTION OF THE DRAWINGS

These and/or other aspects will become apparent and more readily appreciated from the following description of exemplary embodiments, taken in conjunction with the accompanying drawings in which.

DETAILED DESCRIPTION

Reference will now be made in detail to exemplary embodiments, examples of which are illustrated in the accompanying drawings, wherein like reference numerals refer to like elements throughout. In this regard, the present exemplary embodiments may have different forms and should not be construed as being limited to the descriptions set forth herein. Accordingly, the exemplary embodiments are merely described below, by referring to the figures, to explain aspects of the present exemplary embodiments.

The advantages, features and aspects of the exemplary embodiments will become apparent from the following description of the exemplary embodiments with reference to the accompanying drawings, which is set forth hereinafter. The exemplary embodiments may, however, be embodied in different forms and should not be construed as limited to the exemplary embodiments set forth herein. Rather, these exemplary embodiments are provided so that this disclosure will be thorough and complete, and will fully convey the scope of the exemplary embodiments to those of ordinary skill in the art. Like reference numerals refer to like elements throughout.

It will be understood that, although the terms "first", "second", etc. may be used herein to describe various elements, these elements should not be limited by these terms. These terms are only used to distinguish one element from another. For example, a first element could be termed a second element, and, similarly, a second element could be termed a first element, without departing from the scope of the exemplary embodiments.

The terms used herein are for the purpose of describing particular exemplary embodiments only and are not intended to be limiting of exemplary embodiments. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Unless otherwise defined, all terms used herein have the same meaning as commonly understood by one of ordinary skill in the art to which the exemplary embodiments belong. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Hereinafter, a sensor strip cartridge 200, a biometric information measuring apparatus 100 using the same, and a biometric information measuring method using the same according to exemplary embodiments will be described in detail with reference to FIGS. 1 to 15.

Figure 1:
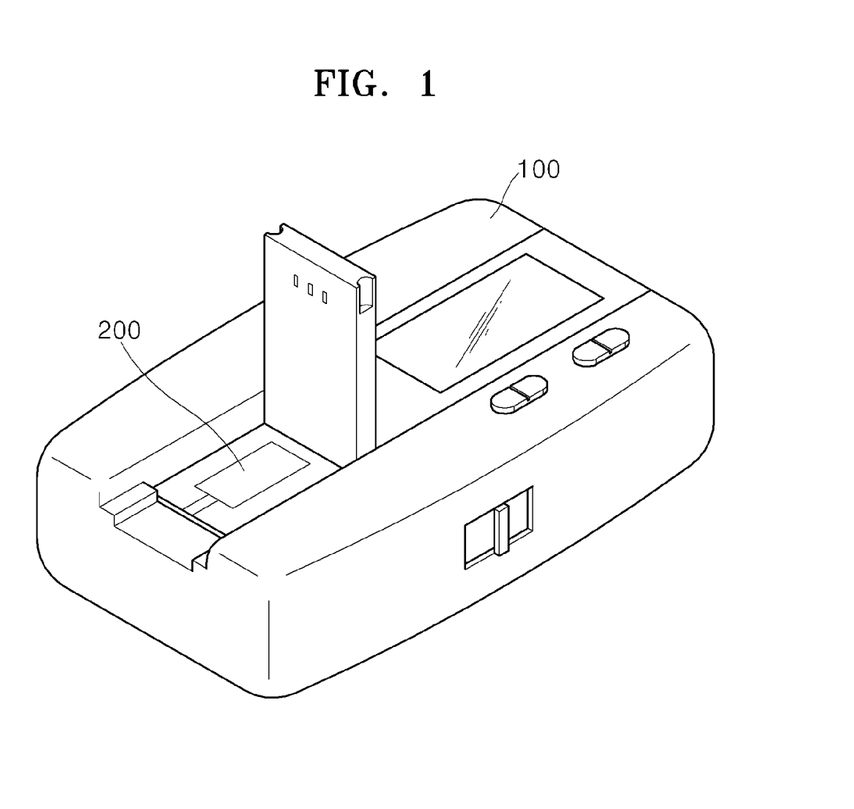
FIG. 1 is a perspective view of a biometric information measuring apparatus according to a first exemplary embodiment.
Figure 2:
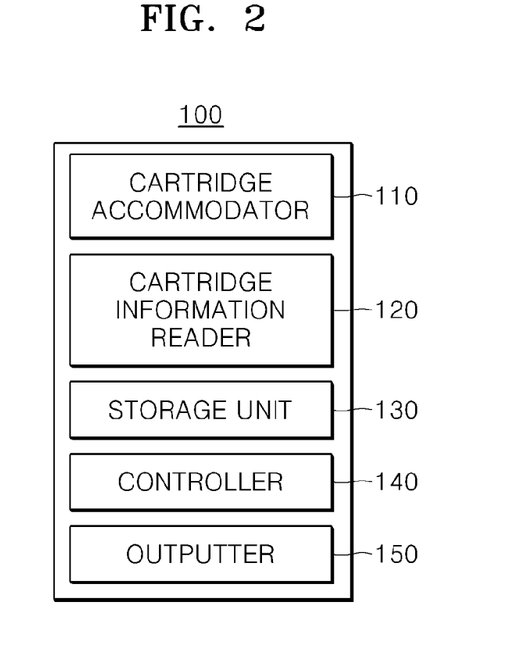
FIG. 2 is a block diagram of the biometric information measuring apparatus according to the first exemplary embodiment.

FIG. 1 is a perspective view of a biometric information measuring apparatus 100 according to a first exemplary embodiment. FIG. 2 is a block diagram of the biometric information measuring apparatus 100 according to the first exemplary embodiment.

Referring to FIGS. 1 and 2, the biometric information measuring apparatus 100 according to the first exemplary embodiment may include a cartridge accommodating unit 110 (e.g., cartridge accommodator) that accommodates a sensor strip cartridge 200 including at least one or more sensor strips, a cartridge information reading unit 120 (e.g., cartridge information reader) that reads cartridge information about the sensor strip cartridge 200 from the sensor strip cartridge 200, a storage unit 130 (e.g., storage) that stores a biometric information correction reference corresponding to the cartridge information, a control unit 140 (e.g., controller) that receives biometric information through the sensor strip and corrects the biometric information by using the biometric information correction reference, and an output unit 150 (e.g., outputter) that outputs the corrected biometric information.

The cartridge accommodating unit 110 may accommodate the sensor strip cartridge 200. According to FIG. 1, a user may accommodate the sensor strip cartridge 200 in the biometric information measuring apparatus 100.

The cartridge accommodating unit 110 may expose the sensor strip included in the sensor strip cartridge 200 to the outside of the biometric information measuring apparatus 100 according to the user's manipulation or a predetermined condition. For example, the sensor strip may measure a blood sugar level from blood. In order for the user to easily coat the sensor strip with blood, the cartridge accommodating unit 110 may expose a portion of the sensor strip which is to be coated with blood to the outside of the biometric information measuring apparatus 100.

Figure 3:
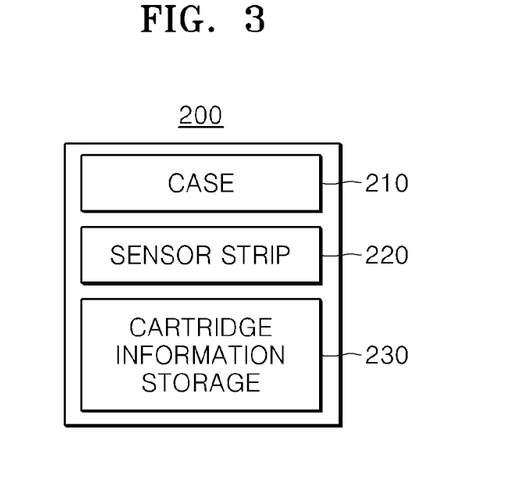
FIG. 3 is a block diagram of a sensor strip cartridge according to a first exemplary embodiment.

FIG. 3 is a block diagram of a sensor strip cartridge 200 according to a first exemplary embodiment. Referring to FIG. 3, the sensor strip cartridge 200 according to the first exemplary embodiment may include a case 210, at least one or more sensor strips 220 which are accommodated in the case 210, and a cartridge information storing unit 230 (e.g., cartridge information storage) that stores cartridge information about the sensor strip cartridge 200.

The case 210 may be provided at an outermost portion of the sensor strip cartridge 200. The case 210 may form an external appearance of the sensor strip cartridge 200. The case 210 may protect the sensor strip 220 and may be formed of a material such as plastic.

At least one or more of the sensor strips 220 may be accommodated in the case 210. The sensor strip 220 may, for example, measure a user's biometric information by using blood. For example, the sensor strip 220 may measure a blood sugar level.

The cartridge information storing unit 230 may store cartridge information. The cartridge information may be information about the sensor strip cartridge 200. For example, the cartridge information may include production information of the sensor strip cartridge 200. The production information of the sensor strip cartridge 200 may include, for example, one or more types of information selected from a manufacturing date, an expiration date, and a manufacturing lot number of the sensor strip cartridge 200.

Moreover, the cartridge information may include information about the sensor strip 220. For example, the cartridge information may include manufacturing information of the sensor strip 220. The manufacturing information of the sensor strip 220 may include, for example, one or more types of information selected from a manufacturing date, an expiration date, and a manufacturing lot number of the sensor strip 220. Also, the cartridge information may include unique code information corresponding to the sensor strip 220. The unique code information may be used to identify the sensor strip 220 or acquire a biometric information correction reference corresponding to the sensor strip 220. In other words, the unique code information may be an identification code of the sensor strip 220.

Referring again to FIG. 2, the cartridge information reading unit 120 may read cartridge information from the sensor strip cartridge 200. The cartridge information reading unit 120 may read cartridge information from the cartridge information storing unit 230 of the sensor strip cartridge 200. A detailed method of reading cartridge information will be described below with reference to FIG. 4.

The storage unit 130 may store a biometric information correction reference corresponding to the cartridge information. A value indicated by the sensor strip 220 may be different per product. For example, the sensor strip 220 may indicate a different value depending on a manufacturing date or a manufacturing lot number of the sensor strip 220. For example, biometric information indicated by the sensor strip 220 may be different depending on the manufacturing lot number of the sensor strip 220. In other words, the biometric information indicated by the sensor strip 220 included in the sensor strip cartridge 200 may be different depending on the cartridge information.

Therefore, the biometric information indicated by the sensor strip 220 may be corrected by using the biometric information correction reference corresponding to the cartridge information. A biometric information correction reference corresponding to each piece of cartridge information may be previously stored in the storage unit 130. The storage unit 130 may, for example, store the biometric information correction reference corresponding to each piece of cartridge information as a mapping table. Also, the biometric information correction reference stored in the storage unit 130 may be corrected or updated according to a user's manipulation or a predetermined condition.

The control unit 140 may receive biometric information from the sensor strip 220. For example, the user may coat an exposed portion of the sensor strip 220 with blood, and the sensor strip 220 may measure biometric information by using the blood. The control unit 140 may receive the measured biometric information from the sensor strip 220.

The control unit 140 may correct the biometric information received from the sensor strip 220. The control unit 140 may correct the received biometric information by using the biometric information correction reference.

By using cartridge information read by the cartridge information reading unit 120, the control unit 140 may acquire a biometric information correction reference corresponding to the cartridge information. For example, the control unit 140 may search for the cartridge information by using the mapping table stored in the storage unit 130, thereby acquiring the biometric information correction reference corresponding to the cartridge information. The control unit 140 may correct biometric information received from the sensor strip 220 by using the acquired biometric information correction reference.

The output unit 150 may output the corrected biometric information. The output unit 150 may, for example, include a display device such as a liquid crystal display (LCD) or an organic light-emitting diode display device. Also, for example, the output unit 150 may include a sound reproducing device such as a speaker. Also, for example, the output unit 150 may include a communication device such as a Bluetooth device, a USB terminal, or a network adaptor.

Hereinafter, detailed configurations of the cartridge information reading unit 120 and the cartridge information storing unit 230 and a method of reading cartridge information will be described in detail.

Figure 4:
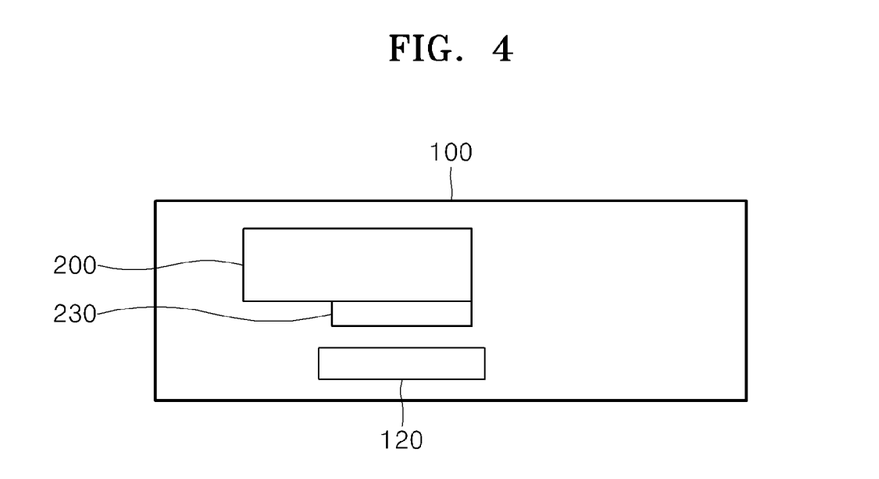
FIG. 4 is a vertical cross-sectional view of a sensor strip cartridge and a biometric information measuring apparatus according to a first exemplary embodiment.

FIG. 4 is a vertical cross-sectional view of the sensor strip cartridge 200 and the biometric information measuring apparatus 100 according to the first exemplary embodiment. Referring to FIG. 4, the cartridge information storing unit 230 may be disposed at one surface of the sensor strip cartridge 200. Also, the cartridge information reading unit 120 may be disposed to face at least one portion of the cartridge information storing unit 230.

The cartridge information storing unit 230 according to the first exemplary embodiment may include a short-distance transmission device. The short-distance transmission device may be, for example, a near field communication (NFC) device, a radio frequency identification (RFID) device, a Bluetooth device, a Zigbee device, or other similar short-distance communication device.

Moreover, the cartridge information reading unit 120 may include a short-distance reception device. The short-distance reception device may be, for example, an NFC device, an RFID device, a Bluetooth device, a Zigbee device, or other similar short-distance reception device.

For example, the cartridge information may be converted into an NFC tag, which may be stored in the cartridge information storing unit 230. When the sensor strip cartridge 200 is accommodated in the cartridge accommodating unit 110, an NFC tag recognizing unit included in the cartridge information reading unit 120 may recognize the NFC tag by using an NFC device included in the cartridge information storing unit 230. Therefore, the cartridge information reading unit 120 may receive cartridge information from the cartridge information storing unit 230.

Moreover, the cartridge information storing unit 230 according to the first exemplary embodiment may include a barcode or a quick response (QR) code. Also, the cartridge information reading unit 120 may include a barcode reader device or a QR code reader device.

For example, the cartridge information may be converted into a barcode or a QR code, which may be stored in the cartridge information storing unit 230. When the sensor strip cartridge 200 is accommodated in the cartridge accommodating unit 110, the barcode reader device or QR code reader device included in the cartridge information reading unit 120 may read the barcode or QR code included in the cartridge information storing unit 230. Therefore, the cartridge information reading unit 120 may receive cartridge information from the cartridge information storing unit 230.

Moreover, the cartridge information storing unit 230 according to the first exemplary embodiment may include a color band including at least one or more colors. Also, the cartridge information reading unit 120 may include a color sensor.

For example, cartridge information may be converted into a color band including at least one or more colors, which may be stored in the cartridge information storing unit 230. When the sensor strip cartridge 200 is accommodated in the cartridge accommodating unit 110, the color sensor included in the cartridge information reading unit 120 may read the color band stored in the cartridge information storing unit 230. Therefore, the cartridge information reading unit 120 may receive cartridge information from the cartridge information storing unit 230.

Figure 5:
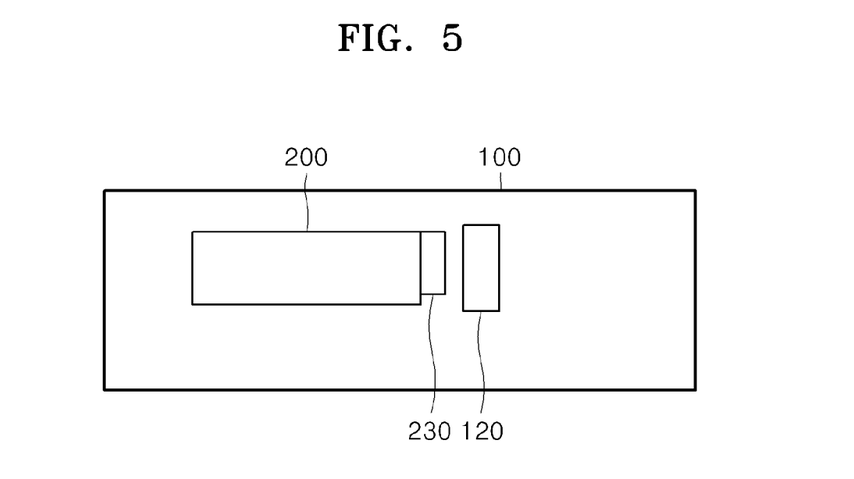
FIG. 5 is a vertical cross-sectional view of a sensor strip cartridge and a biometric information measuring apparatus according to a second exemplary embodiment.

FIG. 5 is a vertical cross-sectional view of a sensor strip cartridge 200 and a biometric information measuring apparatus 100 according to a second exemplary embodiment. In the first exemplary embodiment of FIG. 4, the cartridge information storing unit 230 is illustrated as being disposed under the sensor strip cartridge 200, but as shown in the second exemplary embodiment of FIG. 5, a cartridge information storing unit 230 may be disposed at a side of a sensor strip cartridge 200. In this case, as illustrated in FIG. 5, a cartridge information reading unit 120 may be disposed to face at least one portion of the cartridge information storing unit 230.

Moreover, the cartridge information storing unit 230 is not limited to the exemplary embodiments of FIG. 4 or 5, and may be disposed at an arbitrary portion of the sensor strip cartridge 200.

Figure 6:
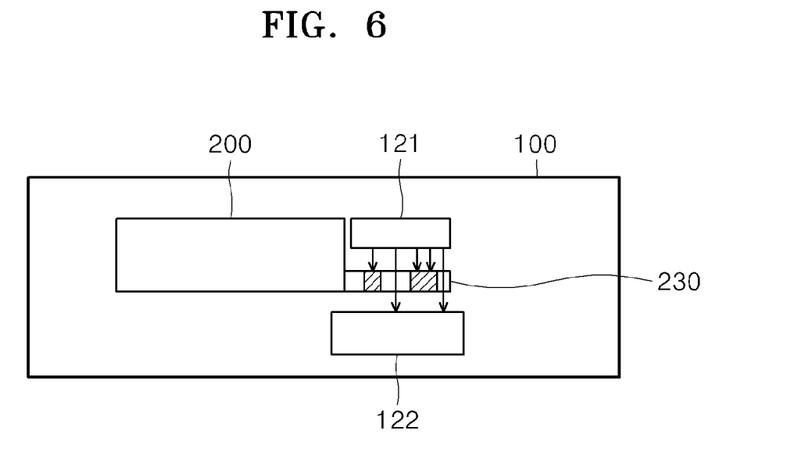
FIG. 6 is a vertical cross-sectional view of a sensor strip cartridge and a biometric information measuring apparatus according to a third exemplary embodiment.

FIG. 6 is a vertical cross-sectional view of a sensor strip cartridge 200 and a biometric information measuring apparatus 100 according to a third exemplary embodiment.

Referring to FIG. 6, the cartridge information storing unit 230 may be disposed at one surface of the sensor strip cartridge 200. The cartridge information storing unit 230 may include a light transmitting layer. Also, the cartridge information reading unit 120 may include an emission unit 121 (e.g., light emitter), which is disposed to face one surface of the light transmitting layer, and a light receiving unit 122 (e.g., light receiver), which is disposed to face another surface opposite the one surface of the light transmitting layer.

As illustrated in FIG. 6, at least one portion of the light transmitting layer of the cartridge information storing unit 230 may be blocked so as not to transmit light. Cartridge information may be converted into a binary number which may be stored in the light transmitting layer. For example, a portion of the light transmitting layer corresponding to the binary number 0 may be blocked so as not to transmit the light, and a portion of the light transmitting layer corresponding to binary number 1 may transmit the light.

When the sensor strip cartridge 200 is accommodated in the cartridge accommodating unit 110, the emission unit 121 included in the cartridge information reading unit 120 may emit light toward the light transmitting layer. Also, the light receiving unit 122 may receive light passing through the light transmitting layer. The light receiving unit 122 may detect a blocked portion and an unblocked portion of the light transmitting layer. Therefore, the cartridge information reading unit 120 may receive cartridge information from the cartridge information storing unit 230.

Figure 7:
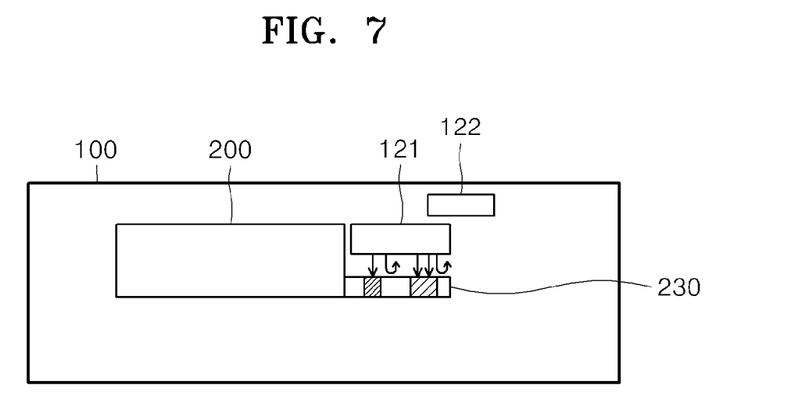
FIG. 7 is a vertical cross-sectional view of a sensor strip cartridge and a biometric information measuring apparatus according to a fourth exemplary embodiment.

FIG. 7 is a vertical cross-sectional view of a sensor strip cartridge 200 and a biometric information measuring apparatus 100 according to a fourth exemplary embodiment.

Referring to FIG. 7, a cartridge information storing unit 230 may be disposed at one surface of the sensor strip cartridge 200. The cartridge information storing unit 230 may include a light reflecting layer. Also, the cartridge information reading unit 120 may be disposed to face one surface of the light reflecting layer. The cartridge information reading unit 120 may include an emission unit 121 and a light receiving unit 122 that receives light which is emitted from the emission unit 121 and reflected by the light reflecting layer.

As illustrated in FIG. 7, at least one portion of the light reflecting layer of the cartridge information storing unit 230 may be blocked so as not to reflect light. Cartridge information may be converted into a binary number which may be stored in the light reflecting layer. For example, a portion of the light reflecting layer corresponding to binary number 0 may be blocked so as not to reflect the light, and a portion of the light reflecting layer corresponding to binary number 1 may allow the light to be reflected.

When the sensor strip cartridge 200 is accommodated in the cartridge accommodating unit 110, the emission unit 121 included in the cartridge information reading unit 120 may emit light toward the light reflecting layer of the cartridge information storing unit 230. Also, the light receiving unit 122 may receive the light reflected by the light reflecting layer. The light receiving unit 122 may read a blocked portion and an unblocked portion of the light transmitting layer. Therefore, the cartridge information reading unit 120 may receive cartridge information from the cartridge information storing unit 230.

Figure 8:
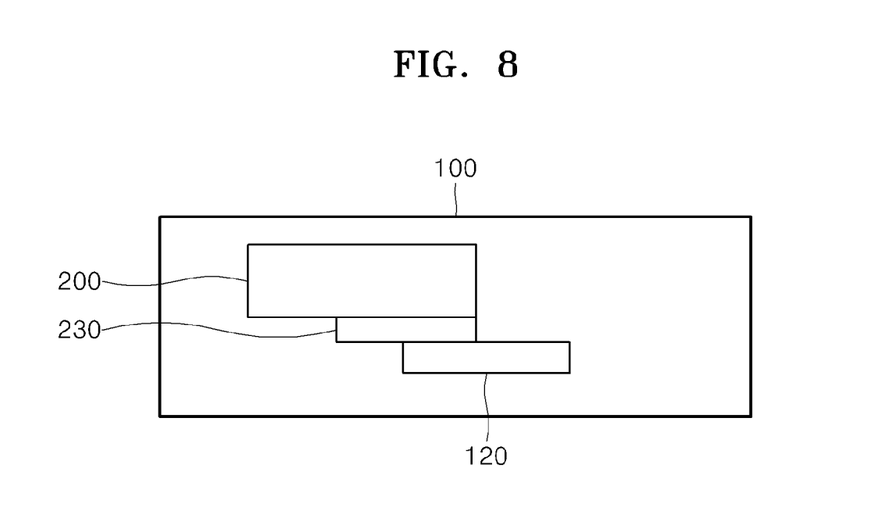
FIG. 8 is a vertical cross-sectional view of a sensor strip cartridge and a biometric information measuring apparatus according to a fifth exemplary embodiment.
Figure 9:
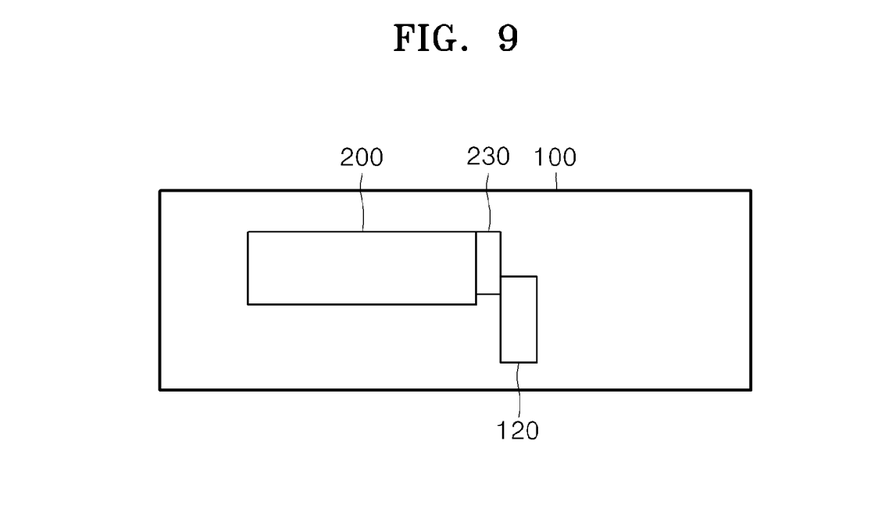
FIG. 9 is a vertical cross-sectional view of a sensor strip cartridge and a biometric information measuring apparatus according to a sixth exemplary embodiment.

FIGS. 8 and 9 are vertical cross-sectional views of a sensor strip cartridge and a biometric information measuring apparatus according to a fifth and sixth exemplary embodiment, respectively.

Referring to FIG. 8, a cartridge information storing unit 230 may be disposed to contact one surface of a sensor strip cartridge 200. Also, referring to FIG. 9, a cartridge information reading unit 120 may be disposed adjacent to at least one portion of the cartridge information storing unit 230.

Figure 10:
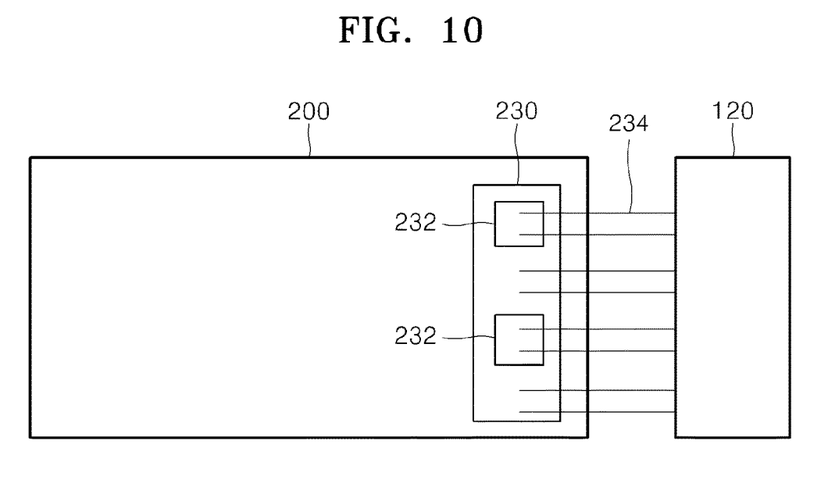
FIG. 10 is a rear view of a sensor strip cartridge and a cartridge information reading unit according to a seventh exemplary embodiment.

FIG. 10 is a rear view of a sensor strip cartridge 200 and a cartridge information reading unit 120 according to a seventh exemplary embodiment. Referring to FIG. 10, a cartridge information storing unit 230 may include at least one or more electrodes 232. Also, the cartridge information reading unit 120 may include at least one or more lines 234 which extend toward the cartridge information storing unit 230.

Cartridge information may be converted into a binary number, which may be stored in the cartridge information storing unit 230. For example, an electrode 232 may be disposed at a portion of the cartridge information storing unit 230 corresponding to binary number 1, and may not be disposed at a portion of the cartridge information storing unit 230 corresponding to binary number 0.

As illustrated in FIG. 10, two lines 234 may be adjacent to each electrode 232. The cartridge information reading unit 120 may apply a voltage to one of the two lines 234 adjacent to each electrode. The voltage may be transferred to the other of the two lines 234. Also, when a voltage is applied to one of two lines 234 extending toward a portion of the sensor strip cartridge 200 at which an electrode 232 is not disposed, the voltage may not be applied to the other of the two lines 234.

When the sensor strip cartridge 200 is accommodated in the cartridge accommodating unit 110, at least one portion of a line 234 included in the cartridge information reading unit 120 may contact the cartridge information storing unit 230. The cartridge information reading unit 120 may apply a voltage to a portion of the line 234. The cartridge information reading unit 120 may detect whether the voltage is applied, via an electrode 232, to the other portion of the line 234 to which the voltage is not applied by the cartridge information reading unit 120. Therefore, the cartridge information reading unit 120 may detect a portion of the cartridge information storing unit 230 where an electrode 232 is disposed, and a portion of cartridge information storing unit 230 where the electrode 232 is not disposed. Therefore, the cartridge information reading unit 120 may receive cartridge information from the cartridge information storing unit 230.

Figure 11:
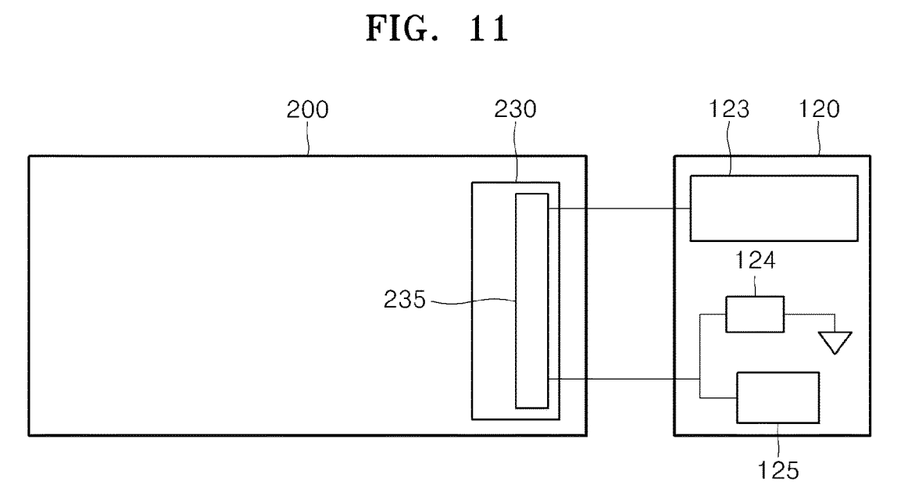
FIG. 11 is a vertical cross-sectional view of a sensor strip cartridge and a biometric information measuring apparatus according to an eighth exemplary embodiment.

FIG. 11 is a rear view of a sensor strip cartridge 200 and a cartridge information reading unit 120 according to an eighth exemplary embodiment. Referring to FIG. 11, a cartridge information storing unit 230 may include at least one resistor 235. A cartridge information reading unit 120 may include a voltage source 123 that is connected to one end of the resistor 235 of the cartridge information storing unit 230 and applies a voltage to the resistor 235, a reference resistor 124 that is connected to the other end of the resistor 235 of the cartridge information storing unit 230 at one end of the reference resistor 124 and is connected to a ground at the other end of the reference resistor 124, and an analog-to-digital converter (ADC) 125 that is connected to the other end of the resistor 235 of the cartridge information storing unit 230.

Cartridge information may be converted into a resistance value corresponding thereto. The resistor 235 included in the cartridge information storing unit 230 may have a resistance value corresponding to the cartridge information. The cartridge information reading unit 120 may apply the voltage to the resistor 235 included in the cartridge information storing unit 230. Also, the cartridge information reading unit 120 may detect the voltage through the ADC 125. A level of the detected voltage changes depending on the resistance value of the resistor 235 included in the cartridge information storing unit 230, and thus, the cartridge information reading unit 120 may acquire the cartridge information from the detected voltage. Therefore, the cartridge information reading unit 120 may receive the cartridge information from the cartridge information storing unit 230.

In the fifth exemplary embodiment of FIG. 8, the cartridge information storing unit 230 is illustrated as being disposed under the sensor strip cartridge 200, but the exemplary embodiments are not limited thereto. For example, as presented in the eighth exemplary embodiment of FIG. 11, a cartridge information storing unit 230 may be disposed at a side of a sensor strip cartridge 200. In this case, as illustrated in FIG. 11, a cartridge information reading unit 120 may be disposed adjacent to face at least one portion of the cartridge information storing unit 230. Detailed configurations of the cartridge information storing unit 230 and the cartridge information reading unit 120 according to the eighth exemplary embodiment may be similar to those of the fifth exemplary embodiment or the sixth exemplary embodiment, or any other exemplary embodiments.

Moreover, the cartridge information storing unit 230 is not limited to the exemplary embodiments of FIG. 8 or 11, and may be disposed at an arbitrary portion of the sensor strip cartridge 200.

Figure 12:
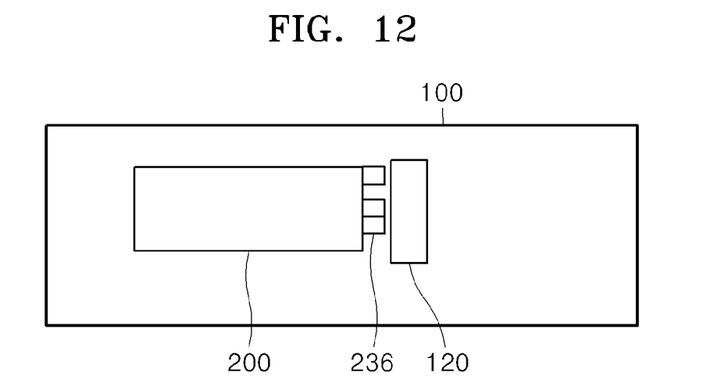
FIG. 12 is a vertical cross-sectional view of a sensor strip cartridge and a biometric information measuring apparatus according to a ninth exemplary embodiment.
Figure 13:
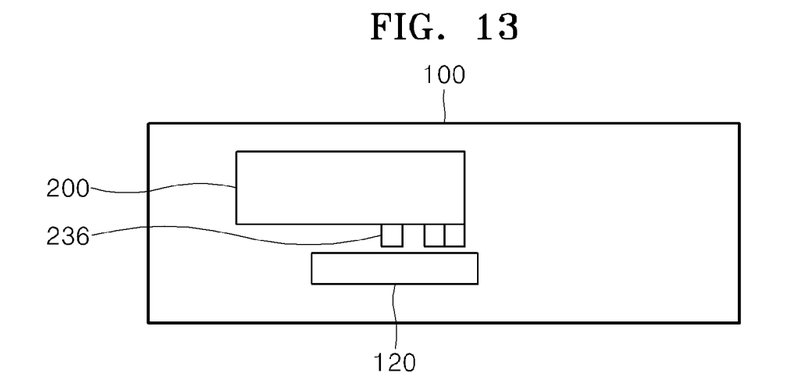
FIG. 13 is an enlarged view of a sensor strip cartridge and a cartridge information reading unit according to a tenth exemplary embodiment.
Figure 14:
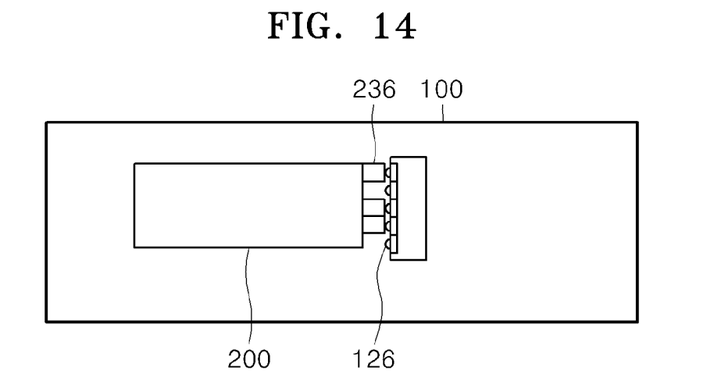
FIG. 14 is a vertical cross-sectional view of a sensor strip cartridge and a biometric information measuring apparatus according to an eleventh exemplary embodiment.

FIGS. 12, 13 and 14 are vertical cross-sectional views of a sensor strip cartridge 200 and a biometric information measuring apparatus 100 according to a ninth, tenth and eleventh exemplary embodiment, respectively. Referring to FIGS. 12 and 13, a cartridge information storing unit 230 may include at least one or more protrusions 236. Also, as shown in FIG. 14, the cartridge information reading unit 120 may include at least one or more switches 126. Each of the switches 126 may be, for example, one selected from a contact type switch, a pressure-sensitive switch, a capacitive switch, and other types of switches.

Cartridge information may be converted into a binary number, which may be stored in the cartridge information storing unit 120. For example, a protrusion 236 may be disposed at a portion of the cartridge information storing unit 230 corresponding to 1 of the binary number. Also, a protrusion may not be disposed at a portion of the cartridge information storing unit 230 corresponding to 0 of the binary number.

As illustrated in FIG. 14, at least some of the switches 126 included in the cartridge information reading unit 120 may contact the protrusion 236 of the cartridge information storing unit 230. In other words, among the switches 126 of the cartridge information reading unit 120, a switch 126 corresponding to a portion of the cartridge information storing unit 230 at which the protrusion 236 is disposed may contact the switch 126 and thereby cause the switch 126 to be switched on. Also, among the switches 126 of the cartridge information reading unit 120, a switch 126 corresponding to a portion of the cartridge information storing unit 230 at which the protrusion 236 is not disposed may not contact the protrusion 236, and thereby cause the switch 126 to be switched off.

Therefore, the cartridge information reading unit 120 may detect a portion of the cartridge information storing unit 230, at which the protrusion 236 is disposed, and a portion of the cartridge information storing unit 230 at which the protrusion 236 is not disposed. Accordingly, the cartridge information reading unit 120 may receive cartridge information from the cartridge information storing unit 230.

In the ninth exemplary embodiment of FIG. 12, the cartridge information storing unit 230 is illustrated as being disposed at a side the sensor strip cartridge 200, but as illustrated in the tenth exemplary embodiment of FIG. 13, a cartridge information storing unit 230 may be disposed under a sensor strip cartridge 200. Detailed configurations of a cartridge information storing unit 230 and a cartridge information reading unit 120 according to the ninth, tenth and eleventh exemplary embodiments may be similar to those in the eighth exemplary embodiments.

Moreover, the cartridge information storing unit 230 is not limited to the exemplary embodiments of FIG. 12 or 13, and may be disposed at an arbitrary portion of the sensor strip cartridge 200. More generally, it is understood that features and aspects of each of the eleven different exemplary embodiments may be combined in many different ways, as would be appreciated by one of ordinary skill in the art.

Figure 15:
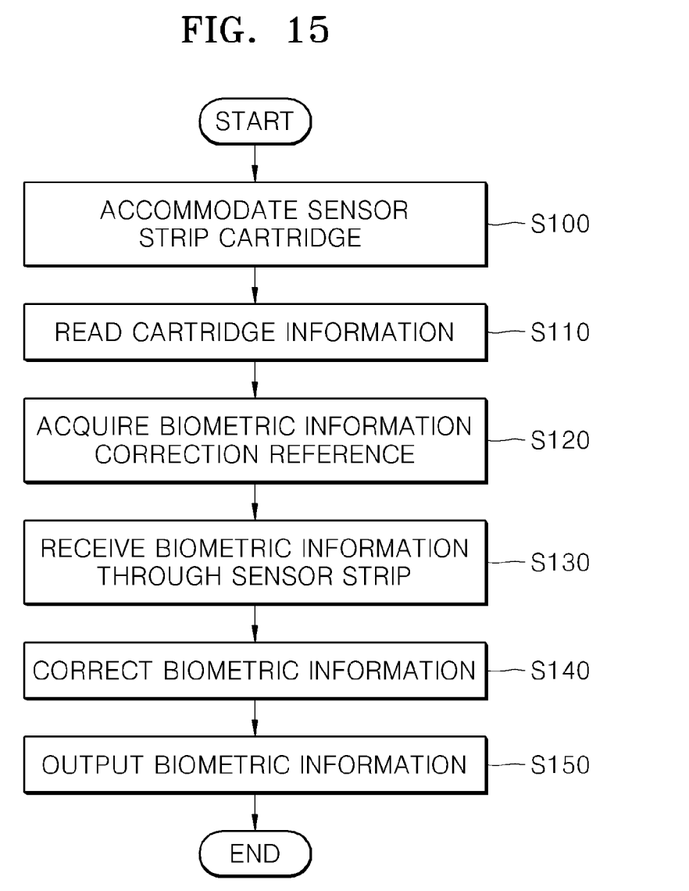
FIG. 15 is a flowchart of a biometric information measuring method according to an exemplary embodiment.

FIG. 15 is a flowchart of a biometric information measuring method according to an exemplary embodiment.

Referring to FIG. 15, in the biometric information measuring method according to an exemplary embodiment, a sensor strip cartridge 200 is accommodated in the biometric information measuring apparatus 100 at operation S100. The sensor strip cartridge 200 may be accommodated in the cartridge accommodating unit 110 of the biometric information measuring apparatus 100.

Subsequently, the biometric information measuring apparatus 100 reads cartridge information about the sensor strip cartridge 200 from the sensor strip cartridge 200 at operation S110. The cartridge information reading unit 120 of the biometric information measuring apparatus 100 may read the cartridge information from the cartridge information storing unit 230 of the sensor strip cartridge 200.

Subsequently, a biometric information correction reference corresponding to the read cartridge information may be acquired at operation S120. The control unit 140 of the biometric information measuring apparatus 100 may acquire the biometric information correction reference corresponding to the cartridge information by using the read cartridge information. For example, the control unit 140 may search for the cartridge information by using a mapping table stored in the storage unit 130.

Subsequently, biometric information may be received through the sensor strip 220 included in the sensor strip cartridge 200 at operation S130. The control unit 140 may receive the biometric information through the sensor strip 220. For example, a user may coat an exposed portion of the sensor strip 200 with blood, and the sensor strip 220 may measure the biometric information by using the blood. The control unit 140 may receive the measured biometric information from the sensor strip 220.

Subsequently, the biometric information may be corrected by using the biometric information correction reference at operation S140. The control unit 140 may correct the biometric information received through the sensor strip 220 by using the acquired biometric information correction reference.

Subsequently, the corrected biometric information may be output at operation S150. The output unit 150 of the biometric information measuring apparatus 100 may output the corrected biometric information.

As described above, according to the one or more of the above exemplary embodiments, the biometric information measuring apparatus may automatically recognize information about a sensor strip.

According to the one or more of the above exemplary embodiments, information about a sensor strip may be automatically recognized even when a user does not directly input manufacturing information of the sensor strip associated with a correction reference for measured biometric information.

According to the one or more of the above exemplary embodiments, a user's convenience increases when the biometric information measuring apparatus including a sensor strip is used.

According to the one or more of the above exemplary embodiments, an error with regard to biometric information is prevented from occurring due to an input error regarding manufacturing information of a sensor strip when the biometric information measuring apparatus is used.

It should be understood that the exemplary embodiments described therein should be considered in a descriptive sense only and not for purposes of limitation. Descriptions of features or aspects within each exemplary embodiment should typically be considered as being available for other similar features or aspects in other exemplary embodiments.

While exemplary embodiments have been described with reference to the figures, it will be understood by those of ordinary skill in the art that various changes in form and details may be made therein without departing from the spirit and scope of the inventive concept as defined by the following claims.

What is claimed is:

1. A biometric information measuring apparatus comprising:
   a cartridge accommodator configured to accommodate a sensor strip cartridge comprising at least one sensor strip;
   a cartridge information reader configured to read cartridge information about the sensor strip cartridge from the sensor strip cartridge;
   a controller configured to receive biometric information through the sensor strip, and correct the received biometric information by using a biometric information correction reference corresponding to the cartridge information; and
   an outputter configured to output the corrected biometric information,
   wherein the sensor strip cartridge comprises at least one protrusion which is disposed in at least one portion of the sensor strip cartridge based on the cartridge information,
   the cartridge information reader comprises at least one switch, and
   the cartridge information reader is configured to detect a switch from the at least one switch which contacts the at least one protrusion, detect a position of the sensor strip cartridge where the at least one protrusion is disposed based on detecting the switch, and read the cartridge information by using the detected position.

2. The biometric information measuring apparatus of claim 1, wherein the cartridge information reader comprises a short-distance communication device configured to receive the cartridge information stored in the sensor strip cartridge from the sensor strip cartridge.

3. The biometric information measuring apparatus of claim 1, wherein the cartridge information reader comprises at least one of a barcode reader device and a quick response (QR) code reader device, and
   the cartridge information reader is configured to read the cartridge information, which is converted into a barcode or a QR code and stored in the sensor strip cartridge, from the sensor strip cartridge.

4. The biometric information measuring apparatus of claim 1, wherein the cartridge information reader comprises a color sensor configured to sense the cartridge information, which is converted into a color band including at least one or more colors and stored in the sensor strip cartridge, from the sensor strip cartridge.

5. The biometric information measuring apparatus of claim 1, wherein the cartridge information reader comprises:
   an emitter that is provided to face a first surface of a light transmitting layer included in the sensor strip cartridge and is configured to emit light; and
   a light receiver that is provided to face a second surface of the light transmitting layer, the second surface being opposite to the first surface, and is configured to receive the light which is emitted from the emitter and passes through the light transmitting layer.

6. The biometric information measuring apparatus of claim 5, wherein at least one portion of the light transmitting layer comprises blocked portions which do not transmit the light based on the cartridge information, and
   the cartridge information reader is configured to detect the blocked portions of the light transmitting layer to thereby read the cartridge information.

7. The biometric information measuring apparatus of claim 1, wherein the cartridge information reader comprises:
   an emitter that is provided to face a surface of a light reflecting layer included in the sensor strip cartridge and configured to emit light; and
   a light receiver configured to receive the light which is emitted from the emitter and reflected by the light reflecting layer.

8. The biometric information measuring apparatus of claim 7, wherein at least one portion of the light reflecting layer comprises blocked portions which do not reflect light based on the cartridge information, and
   the cartridge information reader is configured to detect the blocked portions to thereby read the cartridge information.

9. The biometric information measuring apparatus of claim 1, wherein the sensor strip cartridge comprises an electrode that is disposed in a portion of the sensor strip cartridge based on the cartridge information,
   the cartridge information reader comprises at least two lines that extend toward the sensor strip cartridge, and
   the cartridge information reader is configured to apply a voltage to only a first line among the at least two lines, detect whether the voltage is applied to a second line among the at least two lines by the first line and the electrode, and thereby to detect a position of the sensor strip cartridge where the electrode is disposed, and read the cartridge information by using the detected position.

10. The biometric information measuring apparatus of claim 1, wherein the cartridge information reader comprises:
    a voltage source that is connected to one end of a resistor included in the sensor strip cartridge, and configured to apply a voltage to the resistor;

a reference resistor that is connected to the other end of the resistor at one end of the reference resistor, and is connected to a ground at the other end of the reference resistor; and an analog-to-digital converter (ADC) that is connected to the other end of the resistor, and the resistor has a value corresponding to the cartridge information.

11. The biometric information measuring apparatus of claim 10, wherein the cartridge information reader is configured to read the cartridge information via a level of a voltage detected through the ADC.

12. A biometric information measuring method comprising:

accommodating a sensor strip cartridge in a biometric information measuring apparatus;

reading, by the biometric information measuring apparatus, cartridge information about the sensor strip cartridge from the sensor strip cartridge;

acquiring a biometric information correction reference corresponding to the read cartridge information;

receiving biometric information through a sensor strip included in the sensor strip cartridge;

correcting the biometric information by using the biometric information correction reference; and outputting the corrected biometric information;

wherein the sensor strip cartridge comprises at least one protrusion which is disposed in at least one portion or the sensor strip cartridge based on the cartridge information; and the biometric information measuring apparatus reads the cartridge information by detecting a position of the sensor strip cartridge where the at least one protrusion is disposed and by using the detected position.

13. A biometric measuring device comprising:

a cartridge information reader configured to read cartridge information which identifies a characteristic of a sensor strip cartridge;

a storage configured to store a biometric information correction reference corresponding to the cartridge information; and a controller configured to acquire biometric information from the sensor strip cartridge and correct the biometric information according to the biometric information correction reference;

wherein the sensor strip cartridge comprises a at least one protrusion which is disposed in at least one portion of the sensor strip cartridge based on the cartridge information, the cartridge information reader comprises at least one switch, and the cartridge information reader is configured to detect a switch from the at least one switch which contacts the at least one protrusion, detect a position of the sensor strip cartridge where the at least one protrusion is disposed based on detecting the switch, and read the cartridge information by using the detected position.

14. The biometric measuring device of claim 13, wherein the storage stores a mapping table which maps a plurality of the biometric information correction references to a corresponding plurality of the cartridge information.

* * * * *